(12) United States Patent
Fujimoto et al.

(10) Patent No.: US 7,204,147 B2
(45) Date of Patent: Apr. 17, 2007

(54) ULTRASONIC INSPECTION METHOD FOR WELD ZONE

(75) Inventors: Wataru Fujimoto, Nakatado-gun (JP);
Makoto Yuda, Nakatado-gun (JP);
Kenji Takeuchi, Nakatado-gun (JP)

(73) Assignee: Kawada Industries, Inc., Tokyo (JP)

( * ) Notice: Subject to any disclaimer, the term of this patent is extended or adjusted under 35 U.S.C. 154(b) by 0 days.

(21) Appl. No.: 10/682,317

(22) Filed: Oct. 9, 2003

(65) Prior Publication Data

US 2006/0191343 A1    Aug. 31, 2006

(30) Foreign Application Priority Data

May 9, 2003    (JP) .............................. 2003-131994

(51) Int. Cl.
*G01N 29/032*    (2006.01)

(52) U.S. Cl. .............................. 73/627; 73/598; 73/599; 73/602; 73/628

(58) Field of Classification Search .................. 73/627, 73/624, 625, 628, 629, 619, 620, 621, 622, 73/599, 600, 602, 598
See application file for complete search history.

(56) References Cited

U.S. PATENT DOCUMENTS 3,868,847 A * 3/1975 Gunkel ........................ 73/622
4,160,386 A * 7/1979 Jackson et al. ................ 73/625
4,270,389 A * 6/1981 Shiraiwa et al. .............. 73/612
4,480,475 A * 11/1984 Tsao et al. .................... 73/610
5,005,420 A * 4/1991 Miyajima ..................... 73/629
6,484,584 B2 * 11/2002 Johnson et al. ............... 73/624
6,848,312 B2 * 2/2005 Georgeson ................... 73/627

FOREIGN PATENT DOCUMENTS

| JP | 60-057250 A   |   | 4/1985  |
| JP | 403176658 A   | * | 7/1991  |
| JP | 405172791 A   | * | 7/1993  |
| JP | 2000-310521 A |   | 11/2000 |

* cited by examiner

*Primary Examiner*—Hezron Williams
*Assistant Examiner*—Jacques M Saint-Surin
(74) *Attorney, Agent, or Firm*—Frishauf, Holtz, Goodman & Chick, P.C.

(57) ABSTRACT

An inspection method can easily determine welding condition by just comparing an echo height returned from the weld zone of a real product with a master data.

An master data is made based on the data from prepared test pieces corresponding to the real product.

2 Claims, 5 Drawing Sheets

ULTRASONIC INSPECTION METHOD FOR WELD ZONE

BACKGROUND OF THE INVENTION AND RELATED ART STATEMENT

The present invention relates to an inspection method to evaluate welding condition. The inspection method transmits ultrasonic pulses to a slit as a incomplete penetration in the groove weld zone of a flange and a web.

The inspection method by ultrasonic testing is widely known as a conventional method to evaluate welding condition in the groove weld zone of the flange and the web. The inspection method, which transmits ultrasonic pulses to an object for inspection and then measures the echoes, can specify the location and size of reflection sources in the object based on the echoes. However, the inspection method can not specify the shape, size and angle of flaws precisely in the object.

Generally, the inspection method estimates roughly the size of the each flaw based on the maximum echo and estimates the length of the each flaw as a ultrasonic flaw length based on a dimension where a certain level of the echo is measured. Thus, the inspection method can not measure precisely the depth of the flaw. A new inspection method, which can measure precisely the depth of the flaw, is expected.

As a conventional inspection method to evaluate welding condition in the weld zone, the single probe technique, as disclosed in, for example, Japanese Patent Application KOKAI Publication No. 60-57250 and Japanese Patent Application KOKAI Publication No. 2000-310521, is known.

The inspection method, disclosed in the KOKAI Publication No. 60-57250, transmits ultrasonic pulses from the probe to the weld zone at an angle of 70 degrees, receives the echoes, measures the time and the echo height, and calculates the location of reflection sources by mean of the trigonometric function based on the measured time and the echo height.

However, it is very difficult to acquire high-precision data by this inspection method because this inspection method estimates the location of the reflection source, scans on every side with the probe, and determines the flaw by the echo height. And, although it is comparatively easy to measure the length of the flaw in line with the weld zone, it is very difficult to measure the depth of the flaw by this inspection method because there is no clear inspecting standard and the echoes return from not only the flaws. An experienced operator is required for this inspection method.

Moreover, the inspection method disclosed in the KOKAI Publication No. 2000-310521 is the single probe technique. This inspection method measure the length of an unwelded zone at the point where the maximum echo is measured by transmitting the ultrasonic pulses from the probe, which moves backward and forward on the web, and by receiving the echoes returned from the unwelded zone to the probe. In the Publication, the inspection method is described as the method using the relation that the height of the maximum echo is relative to the length of the unwelded zone.

However, in this inspection method, the echo height does not only depend on the length of the unwelded zone but highly depends on the condition of the contact faces of the flange and the web, such as surface-roughness at the unwelded zone, or the size of a slit when there is a slit at the unwelded zone. Since the condition and the size of the slit cause errors in measuring the length of the unwelded zone by the echo height, this inspection method can not measure precisely.

This inspection method transmits ultrasonic pulses from the end face of the flange to the unwelded zone, and calculates the length of the unwelded zone based on the difference of the arrival time of both echoes, one is returned from the end of the unwelded zone at the tip side of the groove, and the other is returned from the bottom side of the web.

This inspection method measures the length of the unwelded zone by digitizing the echoes and by calculating its digitized numerical values based on certain formulas because the difference of the arrival time of the both echoes is very small. Thus, this inspection method requires accurate processing and special measuring devices, and raises its costs.

Meanwhile, with respect to the evaluation of the quantity of a penetration at the weld zone, a method is conceivable that the actual quantity of the penetration is determined by the information of a incomplete penetration (the slit) by means of the angle beam method with the probe from the outer surface of the web. In this method, a technique is required to recognize the difference of the size of the slit by 0.1 mm.

At the slit, the diffusion and incidence angle of the ultrasonic pulses are important issues because it is difficult to identify the size of the slit and the echoes returned from the slit.

Therefore, a problem that has to be solved is to obtain the best combination, such as the combination of the transducer of the probe, the ultrasonic frequency, the testing position, and the incidence angle of the ultrasonic pulses, etc.

SUMMARY OF THE INVENTION

The present invention was contrived in the view of the problems mentioned above in the ultrasonic inspection method for the weld zone. The present invention therefore aims to provide the inspection method which can measure precisely the height of the slit.

In accordance with the present invention, the following steps are taken.

preparing test pieces, each of said test piece has a slit, said slit has a different height and an almost the same shape as a slit in said weld zone;

transmitting ultrasonic pulses by a probe to said slit in said each test piece and measuring echoes by said probe while moving said probe on said each test piece;

determining a measuring position where an echo height extracted from a measured echo of a basic test piece is clearly distinguished from echo heights extracted from measured echoes of other test pieces;

providing a master data based on said each echo height at said measuring position;

locating said probe at said measuring position on said flange or said web;

transmitting ultrasonic pulses by said probe to said slit in said weld zone and measuring echoes by said probe while moving said probe on said flange or said web;

comparing said measured echoes returned from said weld zone with said master data;

determining a welding condition at said weld zone.

In addition, when said probe is installed in a tracing apparatus which is provided with at least one roller, the present invention can determine the welding condition at the weld zone with maintaining the distance between the weld zone and the probe.

DETAILED DESCRIPTION OF THE PREFERRED EMBODIMENTS

Figure 1:
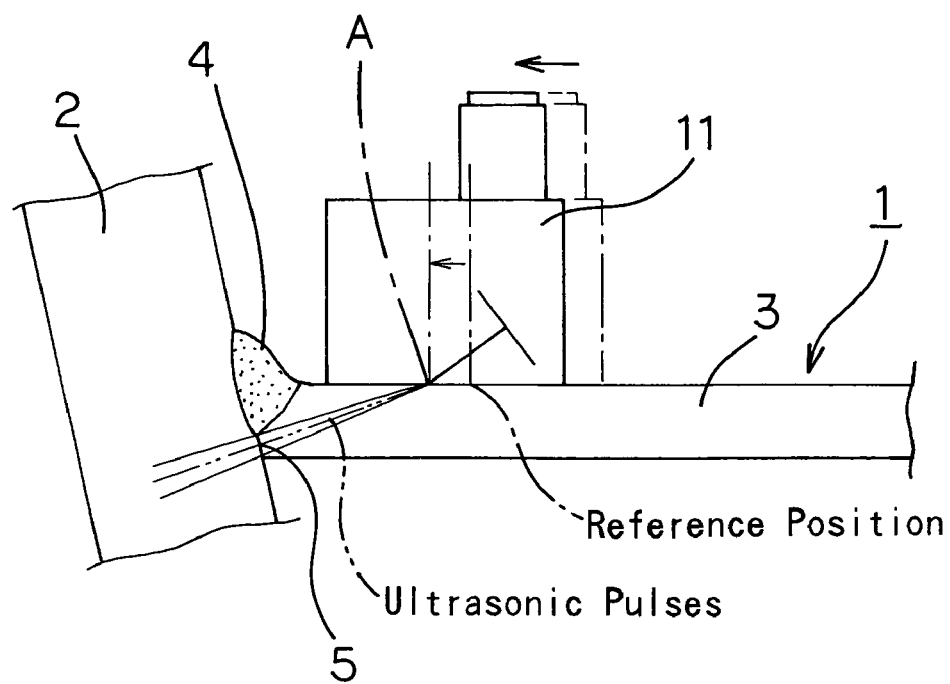
FIG. 1 is a side view showing the inspection method of the present invention on a real product 1.
Figure 2:
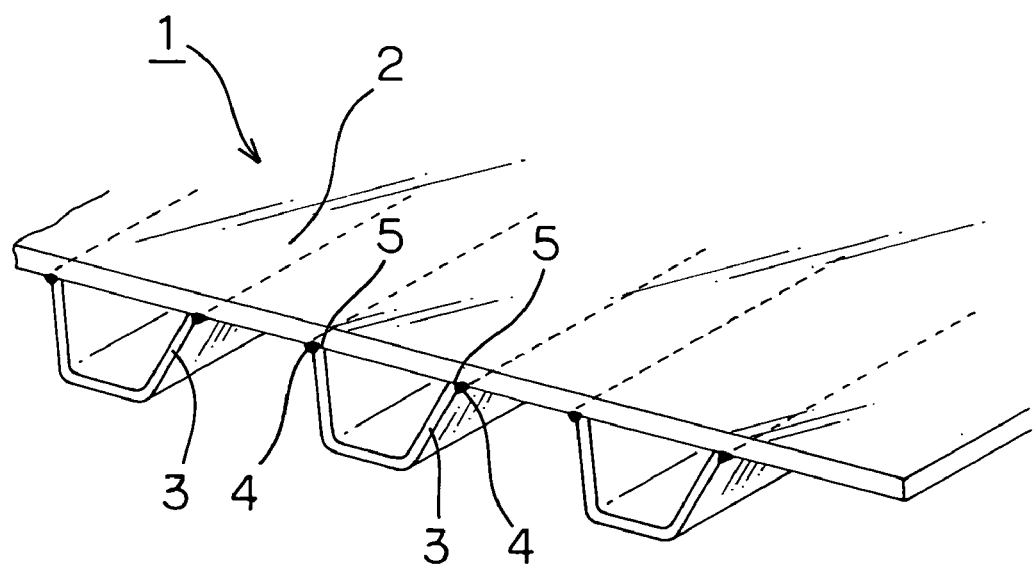
FIG. 2 is a perspective view showing a deck plate 2 and a trough rib 3 as an example of the real product 1.
Figure 3:
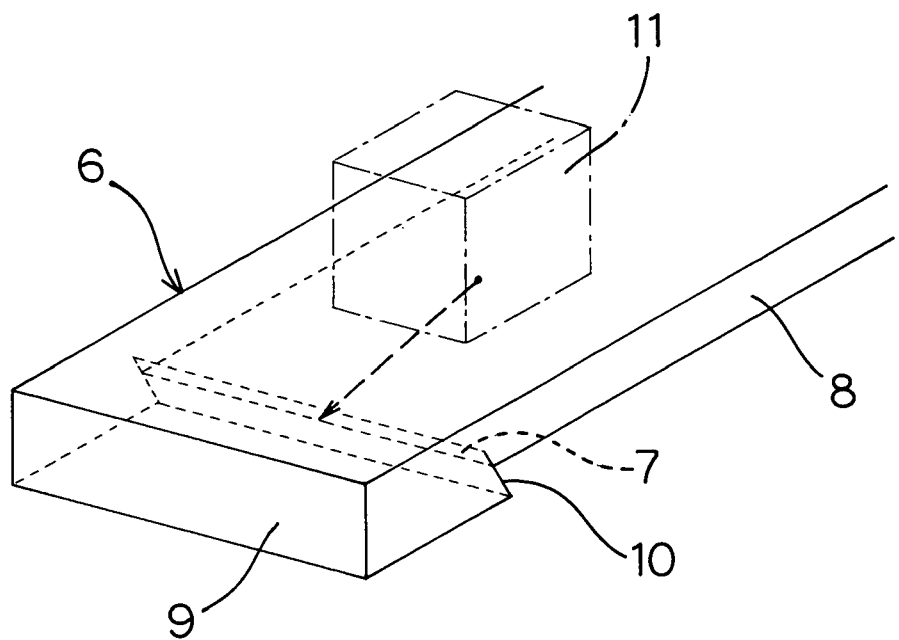
FIG. 3 is a perspective view showing a test piece 6.

The ultrasonic testing method concerning the present invention is described in respect of a preferred embodiment shown in the FIG. 1 and FIG. 2. The method is performed at the weld zone 4, where a deck plate 2 and a trough rib 3 are welded, in the real product 1. At first, test pieces 6 having a slit 7 are prepared. The slit 7, as shown FIG. 3 and FIG. 4, has an almost the same shape as the slit 5 in the weld zone 4.

The each test piece 6 has a block 9 in one end of a base plate 8 having the same thickness as the trough rib 3 (e.g. 8 mm). The block 9 has a inclined plane 10 over against the base plate 8, the inclined plane 10 has the same angle as the slit 5 in the real product 1. The bottom face of the block 9 is projected below the backside of the base plate 8. The slit 7 is formed between the base plate 8 and the block 9.

Since the height of the slit 5 has to be 2.0 mm or less than 2.0 mm when the thickness of the trough rib 3 is 8.0 mm (25% or less than 25% of the thickness of the trough rib 3 is required), ten test pieces 6 having the different height at the slit 7 from 0.3 mm to 5.0 mm are prepared. In these test pieces 6, one test piece 6 which has about 25% of the thickness of the trough rib 3, the height of the slit 7 is 2 mm in the present embodiment, is defined as a basic test piece.

Figure 4:
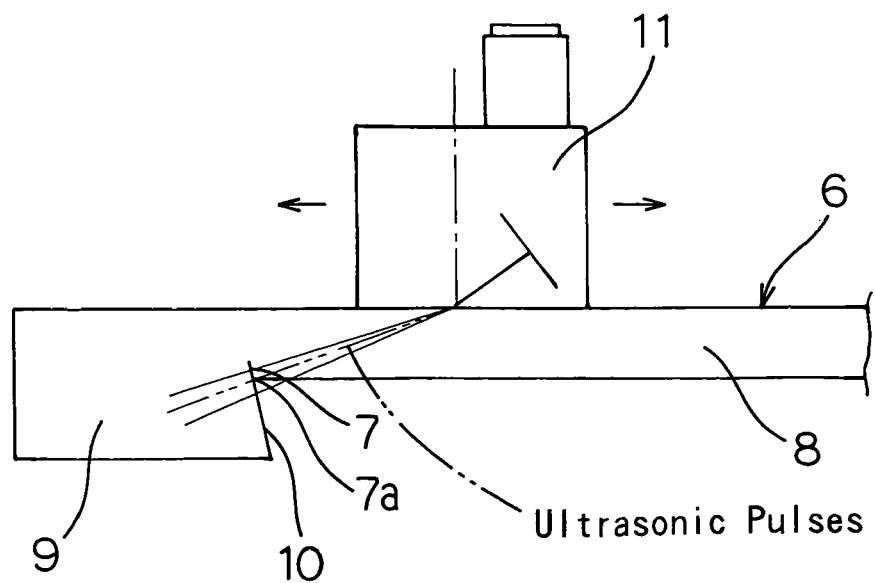
FIG. 4 is a side view showing the test piece 6 and ultrasonic pulses transmitted by a probe 11.

A probe 11, located on the base plate 8 of the each test piece 6 as shown in FIG. 4, transmits ultrasonic pulses to the slit 7 and measures the echo. When measuring the echo, the probe 11 is located at the reference position where the distance between the lower end 7a of the slit 7 and the probe 11 is 0.5 s (Skip). The probe 11 is moved from the reference position to −8.0 mm and to 10.0 mm at intervals of 2.0 mm, and the echo is measured at the each moved position.

Figure 5:
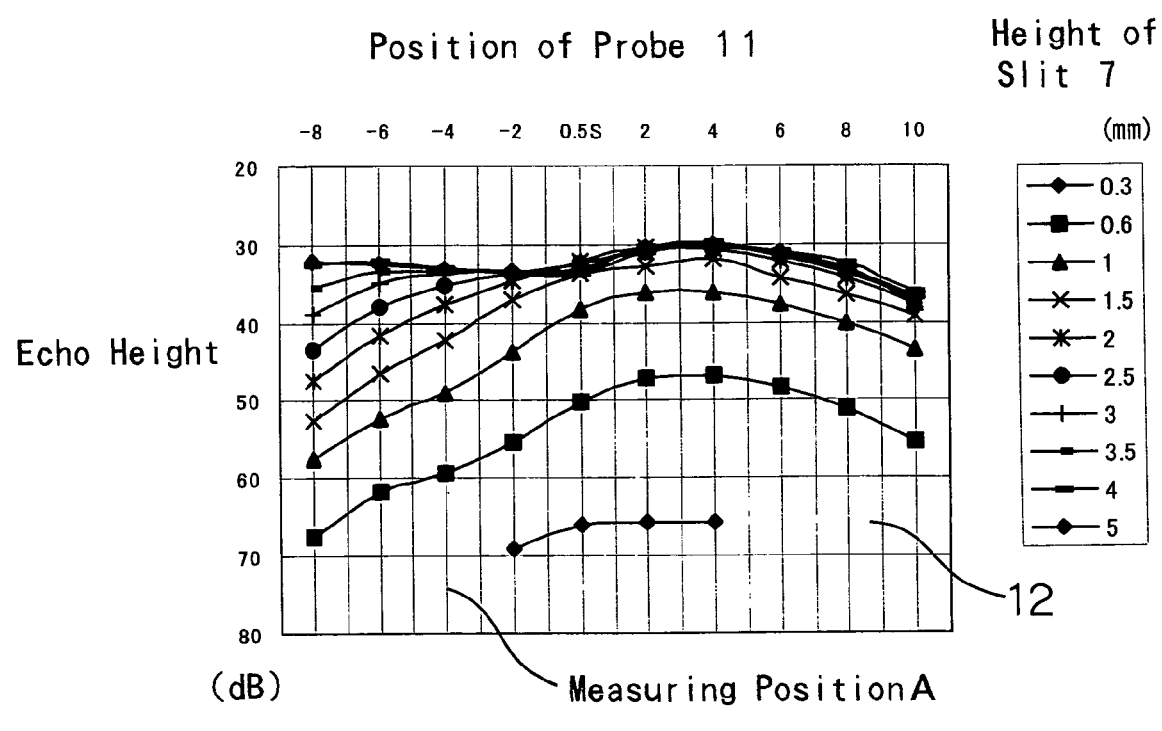
FIG. 5 is a data table 12 showing the echo height of the each test piece 6.

In this way, the echoes at the different positions of the each test piece 6 are measured, the data table 12 as shown FIG. 5 is made.

The data table 12 in FIG. 5 shows the echoes height extracted from the measured echoes at the each measuring position. It is understood that it is more difficult to distinguish the echo height of the basic test piece 6 (the height of the slit 7 is 2 mm) from other test pieces 6 having over 2 mm in the height of the slit 7 at the reference position.

And it is understood that the echo height of the basic test piece 6 clearly distinguished from the echo heights extracted from the measured echoes of other test pieces 6 when the probe 11 is moved from the reference position to −4.0 mm and further.

Moreover, since it is understood that the probe 11 may come in contact with the weld zone 4 in the real product 1 when the probe 11 closes too much to the slit 7, the position moved 4 mm from the reference position to the slit 7 is suitable for the measuring by the probe 11. Therefore, in the present embodiment, the position moved 4 mm from the reference position to the slit 7 is determined as a measuring position A.

Figure 6:
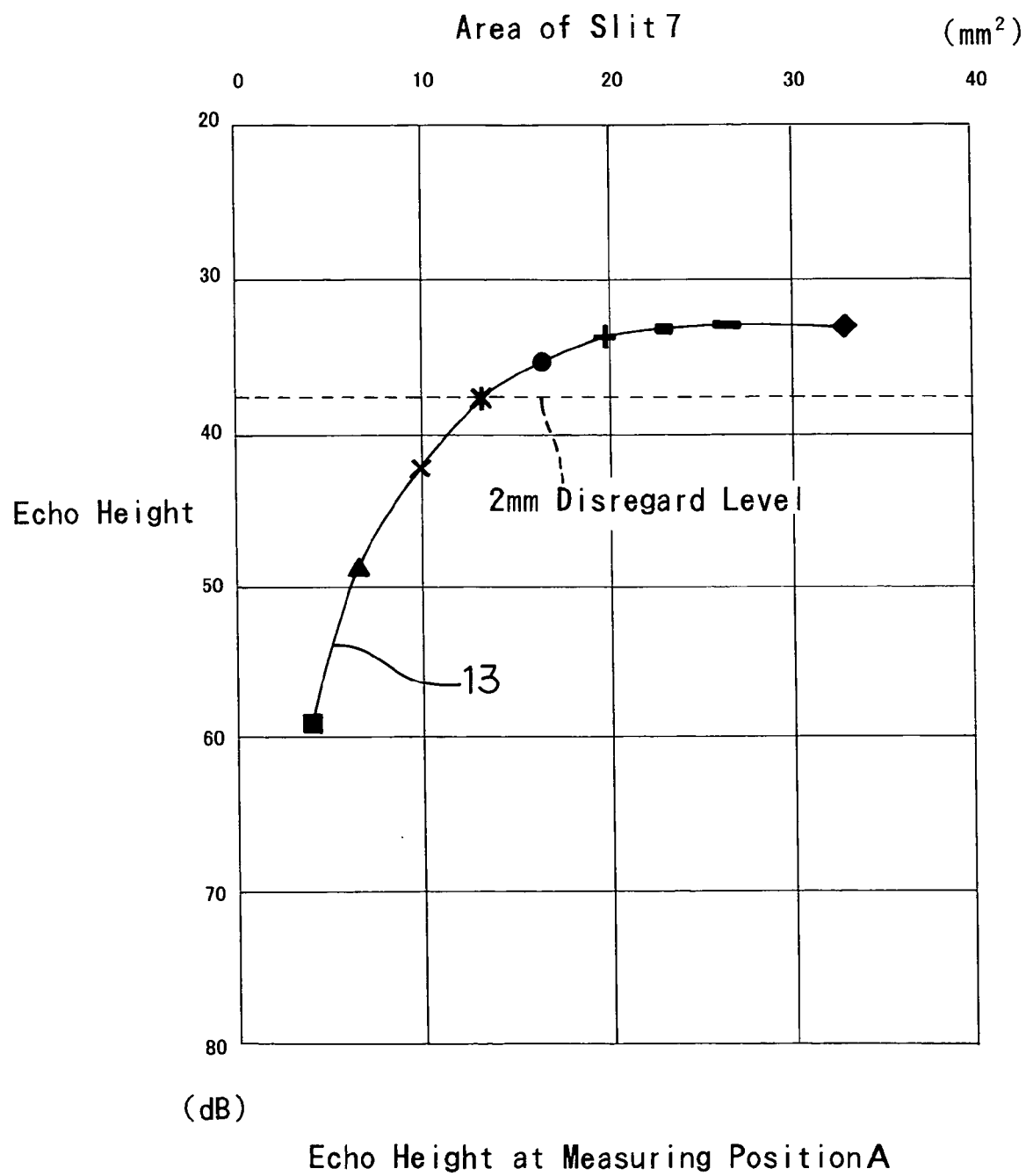
FIG. 6 is a master data 13 showing the echo height at measuring position A.

Next, a master data 13 is prepared as shown in FIG. 6. The master data 13 is provided based on the echo height which is extracted from the measured echo at the measuring position A of the each test piece 6. The master data 13 clearly shows that the height at the unwelded zone is lower than 2 mm when the echo height is higher than 37.6 dB (lower than 2 mm disregard level shown in FIG. 6 as a dotted line).

Then, the probe 11, located at the measuring position A on the trough rib 3 of the real product 1 as shown in FIG. 1, transmits ultrasonic pulses to the weld zone 4 and measures the echo. The measured echo is compared with the master data 13, and the welding condition at the weld zone 4 is determined to be good when the echo height is lower than the 2 mm disregard level because the height of the unwelded zone is lower than the 2 mm.

Figure 7:
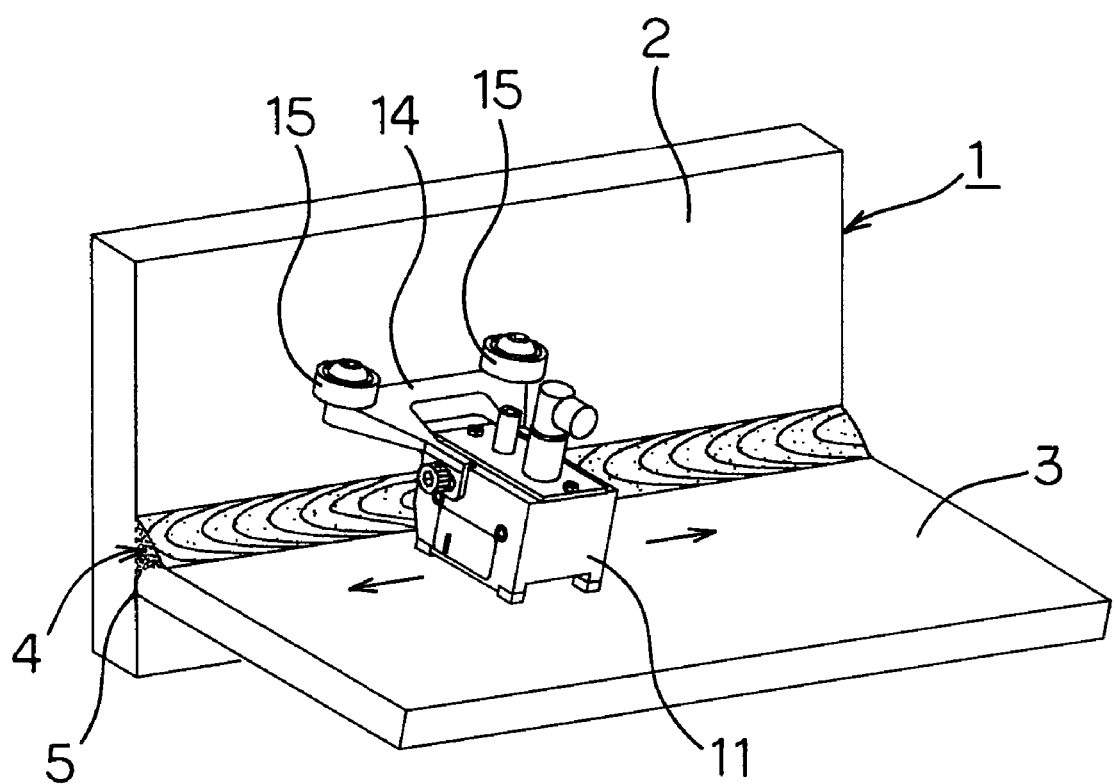
FIG. 7 is a perspective view showing one application of the inspection method of the present invention.

As mentioned above, this inspection method can determine the welding condition at the weld zone 4 with maintaining the distance between the weld zone 4 and the probe 11. Therefore, this inspection method is applicable to apparatuses such as a tracing apparatus 14 as shown in FIG. 7. The tracing apparatus 14, having the probe 11 and rollers 15,15, can inspect the entire welding condition at the weld zone 4, while moving in line with the weld zone 4, by transmitting ultrasonic pulses and by recognizing that the echoes are higher than 37.6 dB.

In addition, as an using example of this inspection method, an automatic welding machine is structured with the probe 11 and a monitor that displays the inspection result. With this structure, the operator of the automatic welding machine can determine the good or bad of the welding condition promptly with watching the monitor.

Moreover, this inspection method is applicable to an inspection for the weld zone of the flange and the web in established constructions, although the inspection method for the weld zone of the deck plate 2 and the trough rib 3 is explained in the above-mentioned embodiment. And, this inspection method is available to an inspection for fatigue cracks in established constructions, although the inspection method in quality control after welding is explained in the above-mentioned embodiment.

In addition, the test piece 6 having 8 mm base plate 8 is prepared in the master data 13 since the thickness of the trough rib 3 in the real product 1 is 8 mm. But even the thickness of the trough rib in the real product is not 8 mm, by means of preparing its test piece corresponding to the trough rib and by means of determining its measurement position based on the pulse angle and the thickness of the base plate of the test piece, its master data is made and the depth of the unwelded zone is measured by just comparing the master data with the echo height returned from the weld zone of the real product.

This inspection method at the weld zone, concerning the present invention as above mentioned, can easily determine the welding condition by just comparing the master data with the echo height returned from the weld zone of the real product, since the master data is made based on the data from the prepared test pieces corresponding to the real product.

In addition, this inspection method can determine the welding condition at the weld zone with maintaining the distance between the weld zone and the probe. Therefore, this inspection method is applicable to a tracing apparatus and can inspect the entire welding condition at the weld zone.

What is claimed is:

1. An ultrasonic inspection method to evaluate a welding condition in a weld zone of a flange and a web of an actual piece to be measured, said method comprising:

preparing test pieces, including a basic test piece, such that each of said test pieces has a slit with substantially a same shape as a slit in the weld zone of the actual piece to be measured, and such that the slit of each of said test pieces has a different height;

transmitting ultrasonic pulses with a probe to said slit and measuring echoes with said probe while positioning the probe at a plurality of measuring positions of each of said test pieces;

determining a measuring position where an echo height extracted from a measured echo of the basic test piece is clearly distinguishable from echo heights extracted from measured echoes of other test pieces at the measuring position;

providing master data based on the echo heights extracted from the measured echoes of each of said test pieces at said determined measuring position;

locating said probe at said determined measuring position on said flange or said web of said actual piece to be measured;

transmitting ultrasonic pulses with said probe to said slit in said weld zone of said actual piece to be measured and measuring echoes with said probe at a plurality of positions on said flange or said web;

comparing said measured echoes returned from said weld zone with said master data;

determining a welding condition at said weld zone based on said comparison.

2. The method as claimed in claim 1, wherein said probe is installed in a tracing apparatus which is provided with at least one roller so as to determine said welding condition of an entirety of the weld zone while maintaining a distance between said weld zone and said probe.

* * * * *